United States Patent
Weihrauch

[11] Patent Number: 6,158,444
[45] Date of Patent: Dec. 12, 2000

[54] INTERDENTAL CLEANER AND MANUFACTURING PROCESS

[75] Inventor: Georg Weihrauch, Wald-Michelbach, Germany

[73] Assignee: Coronet-Werke GmbH, Wald-Michelbach, Germany

[21] Appl. No.: 09/254,674

[22] PCT Filed: Sep. 18, 1997

[86] PCT No.: PCT/EP97/05118

§ 371 Date: Mar. 16, 1999

§ 102(e) Date: Mar. 16, 1999

[87] PCT Pub. No.: WO98/16169

PCT Pub. Date: Apr. 23, 1998

[30] Foreign Application Priority Data

Oct. 15, 1996 [DE] Germany ............................. 196 42 431

[51] Int. Cl.[7] .................................................. A61C 15/00
[52] U.S. Cl. ............................ 132/200; 132/321; 132/329
[58] Field of Search ................................. 132/321, 328, 132/329, 200

[56] References Cited

U.S. PATENT DOCUMENTS

| | | | |
|---|---|---|---|
| 1,527,845 | 2/1925 | Daniel | 132/321 |
| 1,581,501 | 4/1926 | Wright | 132/329 |
| 1,746,591 | 2/1930 | Heymann . | |
| 3,078,856 | 2/1963 | Bender et al. | 132/321 |
| 3,775,848 | 12/1973 | Barnett | 132/329 |
| 3,779,256 | 12/1973 | Maloney et al. | 132/329 |
| 4,319,377 | 3/1982 | Tarrson | 132/321 |
| 4,326,547 | 4/1982 | Verplank | 132/321 |
| 4,832,063 | 5/1989 | Smole | 132/329 |
| 5,775,346 | 7/1998 | Szyszkowski | 132/321 |
| 5,806,540 | 9/1998 | Lee | 132/329 |

FOREIGN PATENT DOCUMENTS

| | | |
|---|---|---|
| 0 161 057 | 11/1985 | European Pat. Off. . |
| 03 54 352 | 2/1990 | European Pat. Off. . |
| 0 707 836 | 4/1996 | European Pat. Off. . |
| 4 54 604 | 7/1913 | France . |
| OS 16 16 134 | 4/1971 | Germany . |
| 42 23 195 | 1/1994 | Germany . |
| 2 11 202 | 11/1940 | Switzerland . |
| 5 89 016 | 9/1947 | United Kingdom . |
| 12 76 031 | 1/1970 | United Kingdom . |
| WO 87 06 452 | 11/1987 | WIPO . |

*Primary Examiner*—Todd E. Manahan
*Attorney, Agent, or Firm*—Paul Vincent

[57] ABSTRACT

In order to ensure a good cleaning of the interdental spaces, an interdental cleaner comprises an elongated, rod-like carrier of a first plastics material, which is covered in partial areas of its surface by at least one insert or support made from a second plastics material, which is softer than the first plastics material. The insert can be placed in a recess formed in the carrier and positively held therein. If the first plastics material of the carrier and/or the second plastics material of the insert or support contains one or more additives, the cleaning and care action can be varied and optimized. For the production of an interdental cleaner, the second plastics material of the insert or support is injection moulded onto the first plastics material of the carrier, the carrier and the insert or support being manufacturable in a two-component injection moulding process.

22 Claims, 5 Drawing Sheets

INTERDENTAL CLEANER AND MANUFACTURING PROCESS

BACKGROUND OF THE INVENTION

The invention relates to an interdental cleaner of a tooth-pick, as well as to a process for the production of a corresponding interdental cleaner or tooth-pick.

For some time it has been scientifically proved that the cleaning of the interdental spaces is of particular significance for keeping healthy the denture and especially the parodontium, because diseases of the gums and also the parodontium, i.e. periodontosis, in most cases emanate from the interdental spaces. A reason for the said diseases is the inadequate cleaning of the interdental spaces and when this occurs osteolytic processes can even arise.

It has been found that it is not possible to adequately clean the interdental spaces with manual or electrical toothbrushes, so that special cleaning devices have to be used. The long known cleaning threads, e.g. dental silk or floss, have not proved successful due to their relatively complicated handling, their relatively limited effects and the risks associated with incorrect use.

For cleaning the interdental spaces, apart from the aforementioned dental silk, nowadays use is made of interdental cleaners in the form of interdental brushes or tooth-picks, the latter being more particularly used for cleaning the slightly open interdental space between bridge anchors and in the sulcus region. Numerous different designs of tooth-picks are known. Wooden tooth-picks are used mainly for removing food residues from the interdental spaces. They can have a round or a triangular cross-section. The round, terminally pointed tooth-picks are particularly suitable for cleaning out pockets. The region of tooth contact points cannot be cleaned with a wooden tooth-pick, so that the risk of caries formation persists.

It is also disadvantageous in connection with wooden tooth-picks, that for stability reasons due to their relatively limited flexural rigidity must have a cross-section or core diameter, which is larger than the openings of the slightly open interdental space, so that they cannot penetrate the narrow cross-section of said space.

EP 277 156 B1 and EP 202 296 B1 in each case discloses an interdental cleaner in the form of a tooth-pick, which has a carrier made from plastic or metal and which for increasing the cleaning action is at least zonally flocked with short polymer fibres. The dimensions of the tooth-pick can be chosen in such a way that even narrow interdental spaces can be carefully cleaned. However, it has been found that the polymer fibres forming the flocking cannot be fixed to the carrier in abrasion-proof manner, so that they can become detached during use, which is found to be very unpleasant by the user. It is also disadvantageous that the additionally applied flock fibres make the tooth-picks excessively thick. However, tooth-picks without flocking have a significantly reduced cleaning action compared with such tooth-picks with flocking. However, after use, it is only possible to inadequately clean food residues or blood in the flocking after use, so that can generally only be used once.

According to EP 277 156 B1 the flocking is provided with cleaning and/or disinfecting agents. However, they only have a short-term effect, because the flock fibres have a relatively large surface for a small volume, so that the introduced agents in a very short time migrate from the inner area of the flock fibres to the surface, where they can be rubbed or washed off.

The problem of the invention is to provide an interdental cleaner and in particular a tooth-pick, which ensures a good cleaning of the interdental spaces and which can be used several times. In addition, a process is to be provided, with which it is possible to rapidly and inexpensively manufacture the interdental cleaner.

With respect to the interdental cleaner the problem is solved in that the interdental cleaner has an elongated, rod-like carrier made from a first plastics material, which in partial areas of its surface is covered by at least one insert or coating made from a second plastics material, which is softer than the first plastics material. This leads to an interdental cleaner, in which on the one hand the stability and on the other the cleaning action are determined by different components or elements, so that each component can be directed in an optimum manner towards its function. The interdental cleaner stability is largely determined by the elongated, rod-like carrier, which is made from the first plastics material. Plastics materials for the carrier are preferably polyamides, polyolefins (e.g. PP/PE homo/copolymers), polyacetals (e.g. POM), polyesters (e.g. partly crystalline forms such as PETP, PBTP, LCP or amorphous forms such as PC), fluorine polymers (e.g. PTFE), polypehnylene sulphides (e.g. PPS), polyether ketones (e.g. PEEK), sulphur polymers (e.g. PSU, PESU), styrene polymers (e.g. PS, SB), polymer blends (e.g. PPO), polyurethanes (e.g. PUR), polyacrylates (e.g. PMMA), polymides (e.g. PEI, PAI), as well as combinations of the aforementioned materials. Optionally said materials can also be finished with long and/or short glass fibre reinforcements. It has been found that a carrier can be obtained which, despite relatively small dimensions, is both adequately stable and also flexible, so that damage to the mucosa is avoided.

SUMMARY OF THE INVENTION

In the interdental cleaner according to the invention the cleaning action is essentially determined by the insert or coating. If the cleaning component is constructed as a coating on the carrier, it is made so thin or flat that it does not significantly increase the dimensions and in particular the thickness of the carrier. However, preferably, the cleaning component is embedded as an insert in the carrier. For this purpose can be constructed a preferably large-surface recess on the carrier surface, into which can be introduced the second plastics material of the insert. Thus, There is an adequate second plastics material quantity, without the dimensions of the interdental cleaner becoming excessive.

According to a possible variant of the invention, the second plastics material of the insert precisely fills the recess without projecting therefrom. Thus, the insert follows the carrier contour and the interdental cleaner dimensions coincide with those of the carrier.

To ensure that the cleaning, second plastics material of the insert or coating engages with the interdental area to be cleaned, it can alternatively be provided that it projects over the carrier, which can e.g. be brought about in that the insert or coating has on at least one side a bulge. Alternatively or additionally thereto on the surface of the insert or coating can be formed a structuring, which increases the cleaning action and additionally exerts a massaging effect.

To avoid sharp edges and the possibly resulting problem of the hooking or sticking of the interdental cleaner, according to a further development of the invention the surface of the insert or coating passes smoothly into the adjacent surface area of the carrier.

As the insert or support does not have to contribute to the stability of the interdental cleaner, its plastics material can be very soft and in particular flexible, which leads to a careful cleaning of the interdental space. In addition, this leads to easy introduceability into narrow gaps, increased contact pressure with good cleaning action and an easy withdrawability, even in the case of jamming between the teeth. As the second plastics material for the insert or coating can in particular be used a thermoplastic elastomer or a plastics material combination.

An increased surface roughness of the thermoplastic elastomer brings about an improved cleaning action, whilst ensuring a careful treatment of the soft tooth material (dentine) prevailing in the area of the interdental space, as well as the gums, the cleaning action being assisted as a result of the rubbing or erasing effect occurring with elastomers (surface material removal during rubbing).

Both the first plastics material of the carrier and the second plastics material of the insert or coating may contain one or more additives. These can e.g. be filling materials assisting cleaning, such as abrasive or non-abrasive fibres (e.g. of PPS), minerals or amorphous-grinding silica abrasives or flavours authorized by the Food and Health Regulations. Moreover, medical constituents such as e.g. fluorine, xylide, antibacterial additives, scale-cleaning substances (NaF), plaque formation-preventing substances or antibiotics can be incorporated. As a result of the small surface/volume ratio of the insert or support achieved according to the invention, it is ensured that additive fractions repeated over a long period of time are concentrated by migration on the surface and during the use of the interdental cleaner of tooth-pick are removed. This ensures a long-lasting activity.

The cross-sectional shape of the carrier can be substantially random, particularly oval, round, triangular or flattened. It must be ensured that the cross-sectional shape, particularly in the interdental cleaner portions penetrating the interdental space, is so chosen that a safe cleaning of narrow interdental spaces is possible. The increase in the cross-sectional surface from the tip of the carrier should be correspondingly chosen. In the longitudinal direction the carrier can either be straight, angled in its tip portion or curved. The cross-sectional shape of the insert or coating can be chosen substantially at random and in particular use can be made of oval, round, flattened or triangular shapes.

The insert or coating is preferably positively fixed to the carrier. As the insert or coating is made from plastic, it can be moulded onto the carrier and can engage behind or through undercuts and/or openings formed on the carrier. This leads to a permanent fixing of the second plastics material to the carrier, which allows a subsequent δ-sterilizability of the interdental cleaner.

Alternatively or additionally, the second plastics material of the insert or coating can be welded to the first plastics material of the carrier, which leads to an improved connection between the materials. As weldable material combinations for the carrier and insert or support use can e.g. be made of PP with a thermoplastic elastomer (TPE) based on EPDM or SEBS, polystyrene with TPE based on SEBS, PP or PE or polyamide with an ionomer or acrylate.

To facilitate the introduction of the interdental cleaner into the interdental space, it and therefore the carrier should taper towards the front end. The front end can be pointed or rounded.

On the carrier the coating or insert can extend to its front end. However, it has been proved particularly advantageous if the insert or coating is set back from the front end of the carrier. Thus, on the first material of the carrier can be formed a particularly thin and stable tip facilitating introduction into the interdental space.

To facilitate for the user the handling and in particular the gripping of the interdental cleaner, at its rear end the carrier should be provided with a grip or handle section, which has a widened gripping surface. The handle can be shaped in one piece onto the carrier. It is alternatively possible to construct the handle as a separate component and the carrier can be detachably fitted thereto. As a result the handle can be reused and, if necessary, fitted with an interdental cleaner.

A sliding of the fingers of the user from the interdental cleaner handle can be prevented if the handle is provided with structuring serving as a gripping aid. The structuring preferably comprises a soft plastics material and for this can in particular be used the second plastics material of the insert or coating, which during the production of the insert support is applied and in particular injection moulded onto the handle. It is additionally possible to use the structuring of the handle as an information carrier, e.g. indicating the manufacturer, product name or product characteristics.

With regards to the process, the set problem is solved in that the second plastics material of the insert or support is injection moulded onto and/or welded to the first plastics material of the carrier. Thus, use is made of a two-component process, in which the supporting and positioning of the relatively thin core forming the carrier can take place through the insert or support forming the second component so as to prevent any bending of the carrier. For supporting the carrier can be used retaining elements, e.g. locking pins, which pass through the second plastics material of the insert or coating, so that holes, slits or openings remain therein, which increase the deformability of the insert or support and form additional cleaning edges.

BRIEF DESCRIPTION OF THE DRAWINGS

Further details and features of the invention can be gathered from the following description of embodiments relative to the attached drawings, wherein show.

DESCRIPTION OF THE PREFERRED EMBODIMENT

Figure 1A:
FIG. 1a A carrier prior to the application of the insert.
Figure 1B:
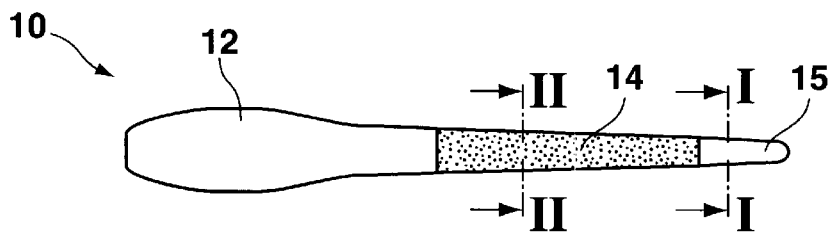
FIG. 1b According to the first embodiment of the invention, in side view.
Figure 1C:
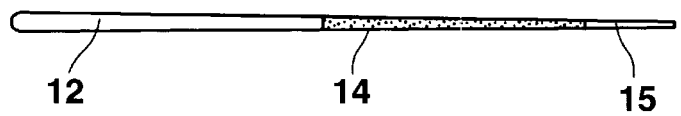
FIG. 1c A plan view of the interdental cleaner of FIG. 1b.

FIGS. 1a to 1e show an elongated, rod-like carrier 11 made from a stable, first plastics material, which is slightly conically tapered in the longitudinal direction towards the front end 15, both with respect to its height and its thickness, and at the front end 15 is rounded. The carrier 11 has an elongated, oval cross-section, as can in particular be gathered from FIG. 1d. At the opposite, rear end, the carrier 11 has a widening serving as a handle 12.

Displaced by a certain distance with respect to the front end 15, the carrier 11 has a reduced size area, so as to form an all-round recess 13. For the formation of an interdental cleaner 10 shown in FIGS. 1b and 1c, the recess 13 is so filled with an insert 14 made from a second plastics material, that between the carrier 11 and insert 14 is provided on all sides a smooth, continuous transition, whilst avoiding steps or edges. The second plastics material of the insert 14 is softer than the first plastics material of the carrier 11 and is specifically intended for obtaining the best possible cleaning action, optionally through corresponding additives.

Figure 1E:
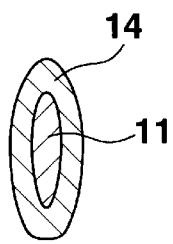
FIG. 1e Section II—II of FIG. 1b.
Figure 1D:
FIG. 1d Section I—I in FIG. 1b.

FIG. 1e shows that the insert 14 completely surrounds the carrier 11 in the region of the recess 13 and is consequently securely held thereon.

Figure 2A:
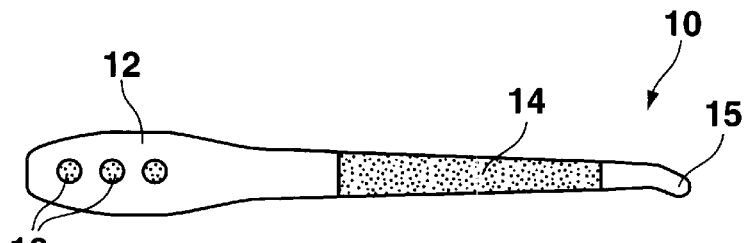
FIG. 2a An interdental cleaner according to a second embodiment in side view.
Figure 2B:
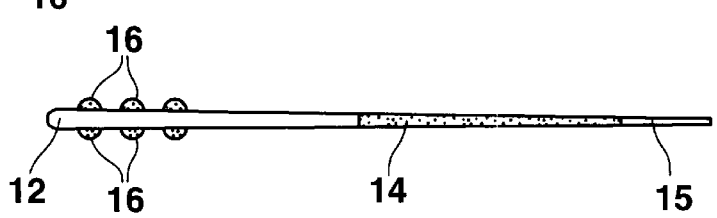
FIG. 2b An interdental cleaner according to a second embodiment in plan view.

The second embodiment shown in FIGS. 2a and 2b has the same basic construction as the interdental cleaner according to the first embodiment and differs therefrom in that the front end 15 of the carrier 11 is slightly angled, so as to permit an easier introduction into the interdental space. In addition, the handle 12 carries a structuring 16, which comprises the second plastics material of the insert 14 and serves as a gripping aid during the use of the interdental cleaner 10.

Figure 3A:
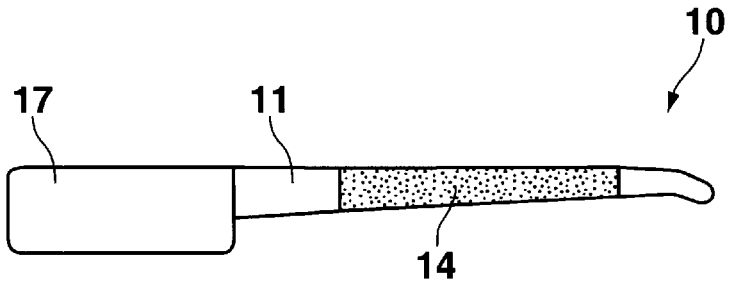
FIG. 3a An interdental cleaner according to a third embodiment in side view.
Figure 3B:
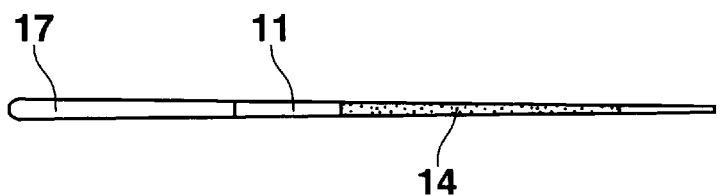
FIG. 3b An interdental cleaner according to a third embodiment in plan view.

In the two aforementioned embodiments, the handle 12 has been shaped in one piece onto the carrier 11. The embodiment shown in FIGS. 3a and 3b shows a reusable handle 17, to which the carrier 11 can be fitted in not shown, detachable manner by means of its rear end and can in particular be plugged or locked in. Following one or several uses of the interdental cleaner 10, the handle 17 can be equipped with a new carrier 11.

Figure 4A:
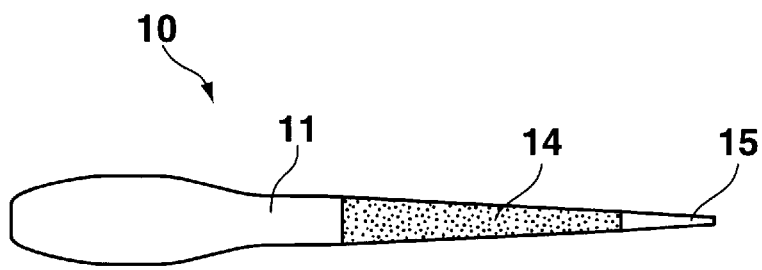
FIG. 4a An interdental cleaner according to a fourth embodiment in side view.
Figure 4B:
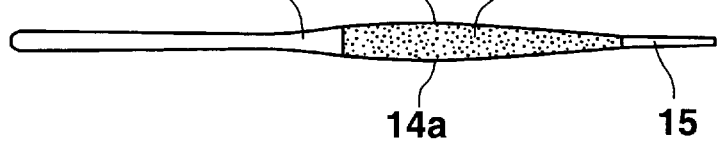
FIG. 4b An interdental cleaner according to a fourth embodiment in plan view.

The interdental cleaner 10 shown in FIGS. 4a and 4b has the same basic construction as in the first embodiment, but here the front end 15 of the carrier 11 tapers. In addition, the insert 14 bends laterally over and beyond the contour of the carrier 11 and on opposite sides forms in each case a bulge 14a, which ensures that the insert 14 on introducing the interdental cleaner 10 into the interdental space to be cleaned, comes into contact with the areas to be cleaned.

Figure 5A:
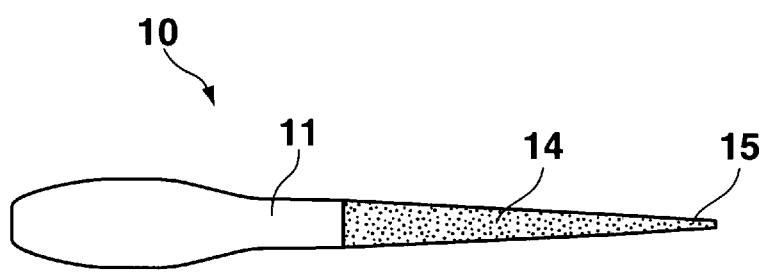
FIG. 5a An interdental cleaner according to a fifth embodiment in side view.
Figure 5B:
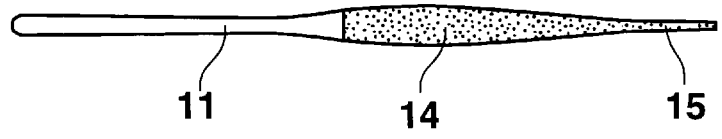
FIG. 5b An interdental cleaner according to a fifth embodiment in plan view.

The interdental cleaner 10 shown in FIGS. 5a and 5b essentially corresponds to the interdental cleaner according to FIGS. 4a and 4b, but the insert 14 extends up to the front end 15 of the carrier 11 and completely surrounds the latter. The insert 14 is held in a not shown, positive manner, e.g. with undercuts or openings, on the carrier 11.

Figure 6A:
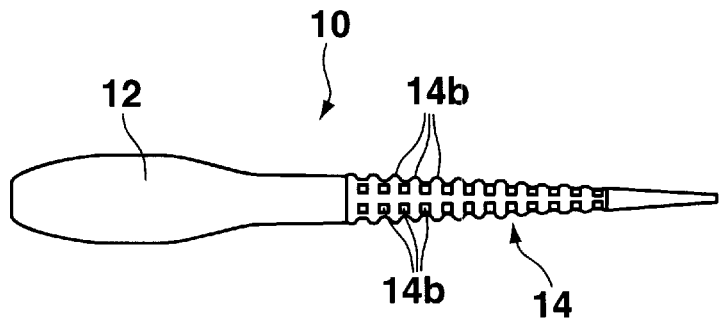
FIG. 6a An interdental cleaner according to a sixth embodiment in side view.
Figure 6B:
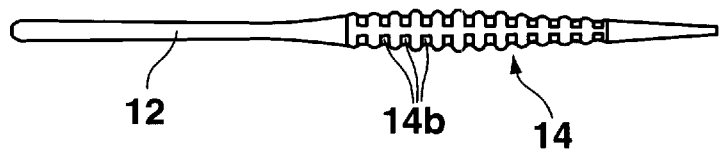
FIG. 6b An interdental cleaner according to a sixth embodiment in plan view.

The embodiment of an interdental cleaner 10 according to FIGS. 6a and 6b also essentially corresponds to that of FIGS. 4a and 4b, but on the outer surface of the insert 14 is formed a structuring in the form of displaced point or knob-like protuberances 14b distributed over the entire circumference. The structuring increases the cleaning action and simultaneously exerts a massaging effect. Alternatively the structuring could be formed by several succeeding, projecting rings in the longitudinal direction of the carrier 11, which extend over the entire circumference or only part thereof and consequently are provided with a circumferential discontinuity.

Figure 7A:
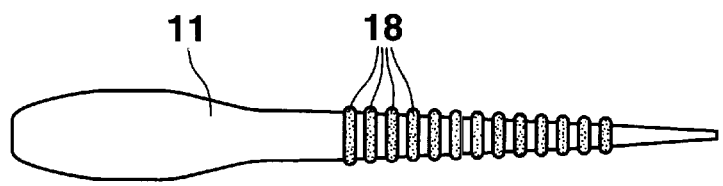
FIG. 7a An interdental cleaner according to a seventh embodiment in side view.
Figure 7B:
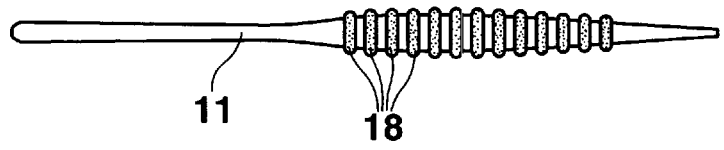
FIG. 7b An interdental cleaner according to a seventh embodiment in plan view.

Whereas in the interdental cleaner according to FIGS. 6a and 6b the surface of the insert 14 is structured, in the case of the interdental cleaner according to FIGS. 7a and 7b there are several annular inserts 18. In its longitudinal direction, the carrier 11 is successively provided with annular recesses, in which is in each case embedded an insert 18 from the softer, second plastics material. On introducing the interdental cleaner 10 into the interdental space to be cleaned, there is consequently an alternation between in each case an insert 18 and the connecting area 11 of the carrier. The inserts 18 project by a small amount over the surface of the carrier 11, which increased the cleaning and massaging action.

Figure 8A:
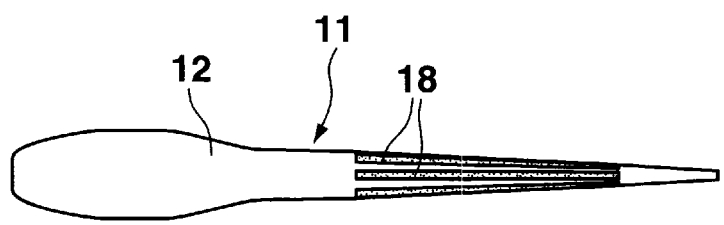
FIG. 8a An interdental cleaner according to a eighth embodiment in side view.
Figure 8B:
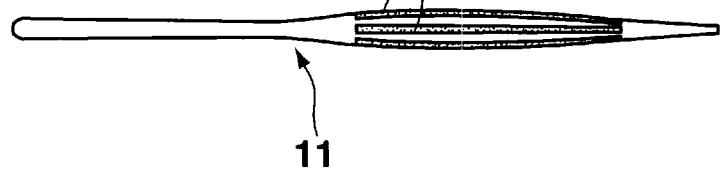
FIG. 8b An interdental cleaner according to a eighth embodiment in plan view.

As a modification of the aforementioned embodiment, in the case of the interdental cleaner according to FIGS. 8a and 8b, there are several inserts 18 running in the longitudinal direction of the carrier 11 and which are preferably identically distributed over the circumference of the carrier 11.

Figure 9A:
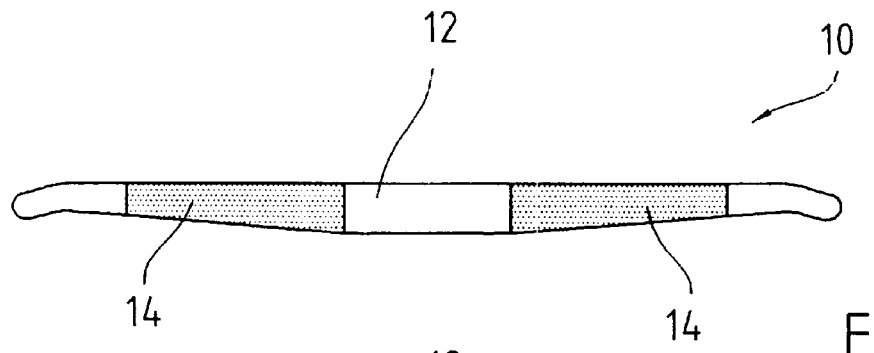
FIG. 9a An interdental cleaner according to a ninth embodiment in side view.
Figure 9B:
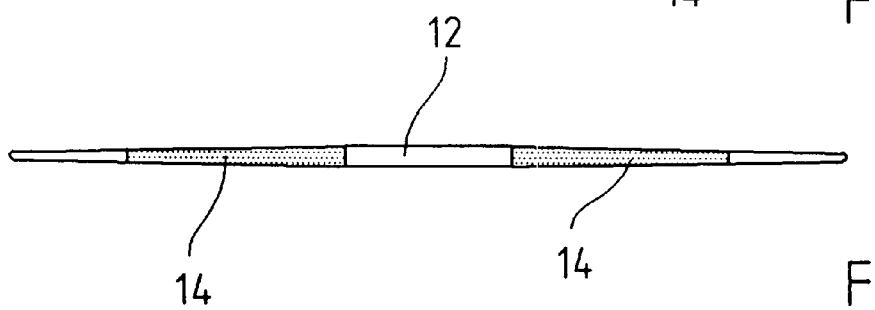
FIG. 9b An interdental cleaner according to a ninth embodiment in plan view.

FIGS. 9a and 9b show an interdental cleaner 10, which has a central handle 12 and, as desired, can be introduced with one of its two ends into an interdental space. On either side of the handle 12 an insert 14 is arranged in the indicated manner. As the interdental cleaner 10 can be introduced by the user, as desired, by one or other end into the interdental space, use can be made of inserts 14 from different materials and/or with different additives.

Figure 10A:
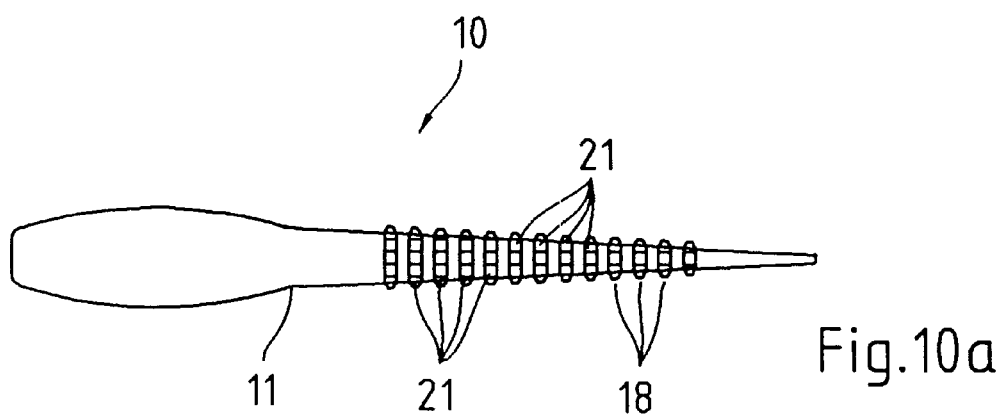
FIG. 10a An interdental cleaner according to a tenth embodiment in side view.
Figure 10B:
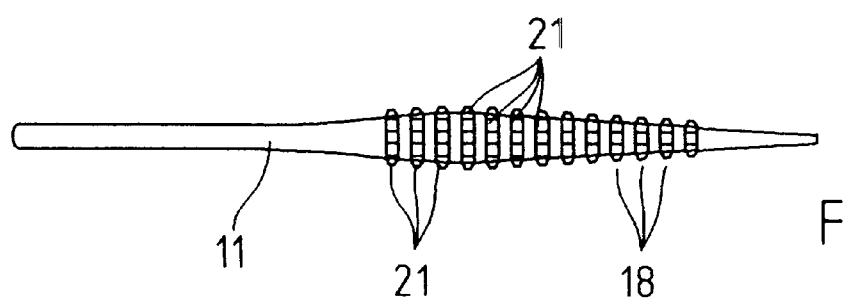
FIG. 10b An interdental cleaner according to a tenth embodiment in plan view.

The interdental cleaner according to FIGS. 10a and 10b differs from the embodiment according to FIGS. 7a and 7b only in that the all-round, annular inserts 18 are additionally provided with an outer structuring in the form of knobs 21.

Figure 11:
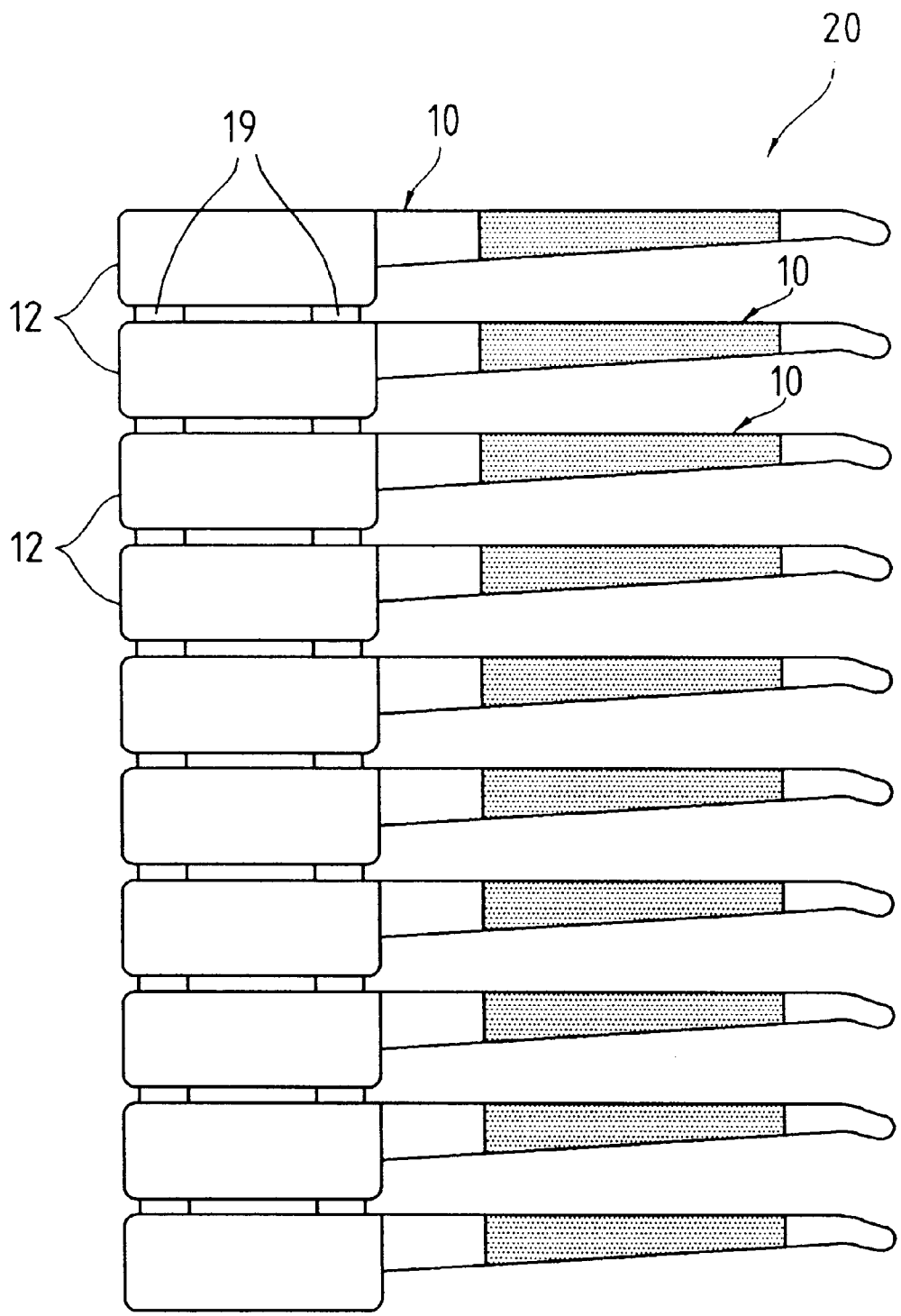
FIG. 11 An arrangement of several interdental cleaners so as to form a cohesive set.

The interdental cleaners can in each case be sold as single items, but it is possible to combine a plurality of interdental cleaners 10 in the manner shown in FIG. 11 so as to form a set 20. The interdental cleaners 10 are juxtaposed with the same orientation, their handles 12 being interconnected by means of webs 19 which can be easily broken off. If a user requires an interdental cleaner 10, he releases the interdental cleaner by breaking the webs 19 from the union, so that the interdental cleaner is separated and can be used.

What is claimed is:

1. A method of manufacturing an interdental cleaner using tow-component injection molding, the method comprising the steps of:
   a) injection molding an elongated rod-shaped carrier from a first plastic material having a first hardness; and
   b) injection molding a thermoplastic elastomer onto said first plastic material to cover at least portions of said first plastic material, said thermoplastic elastomer having a second hardness which is less than said first hardness.

2. The method of claim 1, further comprising fiber reinforcing said first plastic material of said carrier.

3. The method of claim 1, wherein a surface of said thermoplastic elastomer passes smoothly into an adjacent surface area of said carrier.

4. The method of claim 1, wherein said thermoplastic elastomer follows a contour of said carrier.

5. The method of claim 1, wherein said thermoplastic elastomer has a bulge on at least one side thereof.

6. The method of claim 1, wherein said carrier has a recess in which said thermoplastic elastomer is disposed.

7. The method of claim 1, wherein said carrier positively engages and holds said thermoplastic elastomer.

8. The method of claim 1, wherein said carrier has at least one of openings and undercuts which are at least one of penetrated and back-engaged by said thermoplastic elastomer.

9. The method of claim 1, wherein said carrier tapers towards a front end thereof.

10. The method of claim 9, wherein said front end of said carrier is tapered.

11. The method of claim 1, wherein said thermoplastic elastomer is spaced apart from a front end of said carrier.

12. The method of claim 1, wherein said thermoplastic elastomer extends to a front end of said carrier.

13. The method of claim 1, wherein said thermoplastic elastomer is shaped into at least one of protrusions and recesses.

14. The method of claim 13, wherein said protrusions are one of knob-like and bristle-like.

15. The method of claim 1, wherein a rear end of said carrier forms a handle.

16. The method of claim 1, further comprising a handle detachably fit to said carrier.

17. The method of claim 1, further comprising at least one additive contained in at least one of said first plastic material of said carrier and said thermoplastic elastomer.

18. The method of claim 1, further comprising a handle having an embossed surface for at least one of gripping and carrying information.

19. The method of claim 18, wherein said embossed surface consists essentially of said thermoplastic elastomer.

20. A method of manufacturing an interdental cleaner using two-component injection molding, the method comprising the steps of:
   a) injection molding an elongated rod-shaped carrier from a first plastic material having a first hardness; and
   b) injection molding a thermoplastic elastomer onto said first plastic material to cover at least portions of said first plastic material, said thermoplastic elastomer having a second hardness which is less than said first hardness, wherein said thermoplastic elastomer is welded to said first plastic material.

21. A method of manufacturing an interdental cleaner using two-component injection molding, the method comprising the steps of:
   a) injection molding an elongated rod-shaped carrier from a first plastic material having a first hardness;
   b) supporting said carrier with retaining elements; and
   c) injection molding a thermoplastic elastomer onto said first plastic material and said retaining elements to cover at least portions of said first plastic material, said thermoplastic elastomer having a second hardness which is less than said first hardness, wherein said retaining elements pass through said thermoplastic elastomer.

22. A method of manufacturing an interdental cleaner using two-component injection molding, the method comprising the steps of:
   a) injection molding an elongated rod-shaped carrier from a first plastic material having a first hardness, said elongated carrier having a handle portion and an elongated, tapered member integral with said handle portion, said elongated, tapered member having a recess fashioned about a periphery thereof;
   b) injection molding a thermoplastic elastomer onto said elongated, tapered member to fill said recess, said thermoplastic elastomer having a second hardness which is less than said first hardness, said injection molded thermoplastic elastomer having a continuous, smooth outer surface mapping smoothly and without steps into a surface of said elongated, tapered member adjacent to said recess.

* * * * *

(12) EX PARTE REEXAMINATION CERTIFICATE (10393rd)
United States Patent
Weihrauch

(10) Number: US 6,158,444 C1
(45) Certificate Issued: Nov. 12, 2014

(54) INTERDENTAL CLEANER AND MANUFACTURING PROCESS

(75) Inventor: Georg Weihrauch, Wald-Michelbach (DE)

(73) Assignee: Interbros GmbH

Reexamination Request:
No. 90/013,097, Jan. 22, 2014

Reexamination Certificate for:
Patent No.: 6,158,444
Issued: Dec. 12, 2000
Appl. No.: 09/254,674
Filed: Mar. 16, 1998

(21) Appl. No.: 90/013,097

(22) PCT Filed: Sep. 18, 1997

(86) PCT No.: PCT/EP97/05118
§ 371 (c)(1),
(2), (4) Date: Mar. 16, 1999

(87) PCT Pub. No.: WO98/16169
PCT Pub. Date: Apr. 23, 1998

(30) Foreign Application Priority Data

Oct. 15, 1996 (DE) .................................. 196 42 431

(51) Int. Cl.
*A61C 15/00* (2006.01)
*A61C 15/02* (2006.01)

(52) U.S. Cl.
CPC ................. *A61C 15/02* (2013.01); *A61C 15/00* (2013.01)
USPC ............................ 132/200; 132/321; 132/329

(58) Field of Classification Search
None
See application file for complete search history.

(56) References Cited

To view the complete listing of prior art documents cited during the proceeding for Reexamination Control Number 90/013,097, please refer to the USPTO's public Patent Application Information Retrieval (PAIR) system under the Display References tab.

*Primary Examiner* — Cary Wehner

(57) ABSTRACT

In order to ensure a good cleaning of the interdental spaces, an interdental cleaner comprises an elongated, rod-like carrier of a first plastics material, which is covered in partial areas of its surface by at least one insert or support made from a second plastics material, which is softer than the first plastics material. The insert can be placed in a recess formed in the carrier and positively held therein. If the first plastics material of the carrier and/or the second plastics material of the insert or support contains one or more additives, the cleaning and care action can be varied and optimized. For the production of an interdental cleaner, the second plastics material of the insert or support is injection moulded onto the first plastics material of the carrier, the carrier and the insert or support being manufacturable in a two-component injection moulding process.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 22 is cancelled.

Claims 1, 20 and 21 are determined to be patentable as amended.

Claims 2-19, dependent on an amended claim, are determined to be patentable.

New claims 23-25 are added and determined to be patentable.

1. A method of manufacturing an interdental cleaner using [tow-component] *two-component* injection molding, the method comprising the steps of:
   a) injection molding an elongated rod-shaped carrier from a first plastic material having a first hardness; and
   b) injection molding a thermoplastic elastomer *to weld said thermoplastic elastomer* onto said first plastic material [to] *and* cover at least portions of said first plastic material, said thermoplastic elastomer having a second hardness which is less than said first hardness.

20. A method of manufacturing an interdental cleaner using two-component injection molding, the method comprising the steps of:
    a) injection molding an elongated rod-shaped carrier from a first plastic material having a first hardness; and
    b) injection molding a thermoplastic elastomer onto said first plastic material to cover at least portions of said first plastic material, said thermoplastic elastomer having a second hardness which is less than said first hardness, wherein *injection molding* said thermoplastic elastomer [is welded] *welds the thermoplastic elastomer* to said first plastic material.

21. A method of manufacturing an interdental cleaner using two-component injection molding, the method comprising the steps of:
    a) injection molding an elongated rod-shaped carrier from a first plastic material having a first hardness;
    b) supporting said carrier with retaining elements; [and]
    c) injection molding a thermoplastic elastomer onto said first plastic material and said retaining elements to cover at least portions of said first plastic material *and to weld said thermoplastic elastomer to said first plastic material*, said thermoplastic elastomer having a second hardness which is less than said first hardness[, wherein said retaining elements pass through said thermoplastic elastomer]*; and*
    *d) removing the retaining elements to form openings in the thermoplastic elastomer and increase the deformability of the interdental cleaner.*

*23. The method of claim 21, wherein the retaining elements comprises locking pins.*

*24. The method of claim 21, wherein the openings in the thermoplastic elastomer form additional cleaning edges.*

*25. A method of manufacturing an interdental cleaner using two-component injection molding, the method comprising:*
   *a) injection molding a first plastic material having a first hardness to form an elongated rod-shaped carrier;*
   *b) supporting the carrier using at least one retaining element;*
   *c) injection molding a thermoplastic elastomer to form an insert and weld the insert onto at least portions of the carrier, wherein the thermoplastic elastomer is injection molded onto the retaining element and the thermoplastic elastomer has a second hardness that is less than the first hardness; and*
   *d) removing the retaining element to form openings in the insert, wherein the openings increase the deformability of the interdental cleaner and form additional cleaning edges on the insert.*

* * * * *